US006296196B1

(12) United States Patent

Denen et al.

(10) Patent No.: US 6,296,196 B1

(45) Date of Patent: Oct. 2, 2001

(54) CONTROL SYSTEM FOR ATOMIZING LIQUIDS WITH A PIEZOELECTRIC VIBRATOR

(75) Inventors: Dennis J. Denen; Gary E. Myers, both County of Franklin; Leon M. Headings, County of Wayne; George A. Clark; Eric R. Navin, both County of Delaware; Todd L. James, County of Franklin, all of OH (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/519,560

(22) Filed: Mar. 6, 2000

Related U.S. Application Data

(60) Provisional application No. 60/124,155, filed on Mar. 5, 1999.

(51) Int. Cl.[7] .............................. B05B 17/04; B05B 1/08; B05B 3/04

(52) U.S. Cl. .......................... 239/4; 239/102.1; 239/102.2

(58) Field of Search .............................. 239/102.1, 102.2, 239/145, 326, 338, 4; 310/314–316, 316.01, 328

(56) References Cited

U.S. PATENT DOCUMENTS

| | | | | |
|---|---|---|---|---|
| 3,543,122 | | 11/1970 | Klebanoff et al. | 318/443 |
| 3,615,041 | | 10/1971 | Bischoff . | |
| 3,738,574 | | 6/1973 | Gunterdorfer et al. . | |
| 4,113,809 | | 9/1978 | Abair et al. . | |
| 4,338,576 | | 7/1982 | Takahashi et al. | 331/67 |
| 4,473,187 | * | 9/1984 | Lierke et al. | 239/102 |
| 4,479,609 | | 10/1984 | Maeda et al. | 239/102 |
| 4,533,082 | | 8/1985 | Maehara et al. | 239/102 |
| 4,533,735 | | 8/1985 | Walter | 546/156 |
| 4,632,311 | | 12/1986 | Nakane et al. | 239/101 |
| 4,641,053 | | 2/1987 | Takeda . | |
| 4,659,014 | * | 4/1987 | Soth et al. | 239/102.2 |
| 4,689,515 | * | 8/1987 | Benndorf et al. | 310/316 |
| 4,702,418 | | 10/1987 | Carter et al. | 239/101 |
| 4,790,479 | | 12/1988 | Matsumoto et al. | 239/102.2 |
| 5,152,456 | * | 10/1992 | Ross et al. | 239/102.2 |
| 5,164,740 | | 11/1992 | Ivri | 346/1.1 |
| 5,297,734 | | 3/1994 | Toda | 239/102.2 |
| 5,312,280 | | 5/1994 | Kloba et al. | 445/59 |
| 5,312,281 | * | 5/1994 | Takahashi et al. | 446/25 |
| 5,343,122 | | 8/1994 | Sugimori et al. | 315/209 R |
| 5,487,378 | | 1/1996 | Robertson et al. . | |
| 5,518,179 | | 5/1996 | Humberstone et al. | 239/102.2 |
| 5,657,926 | | 8/1997 | Toda | 239/102.1 |
| 5,716,002 | * | 2/1998 | Haack et al. | 239/102.2 |
| 5,803,362 | | 9/1998 | Fraccaroli | 239/102.2 |
| 5,938,117 | | 8/1999 | Ivri . | |

FOREIGN PATENT DOCUMENTS

| | | | |
|---|---|---|---|
| 0 123 277 A2 | 10/1984 | (EP) | 84/44 |
| 0123277A | 10/1984 | (EP) . | |
| 58109156 | 6/1983 | (JP) . | |
| WO92/11050 | 7/1992 | (WO) . | |

* cited by examiner

*Primary Examiner*—David A. Scherbel
*Assistant Examiner*—Davis Hwn

(57) ABSTRACT

There is described a battery driven atomizer in which an alternating voltage is applied to a piezoelectric actuation element to cause it to expand and contract and vibrate an atomizing orifice plate. The alternating voltage is controlled to produce a high amplitude vibration during a first portion of a drive period, to initiate atomization, and thereafter to produce a lower amplitude vibration to sustain atomization during the remainder of the drive period. The frequency of the alternating voltage is swept repeatedly during each drive period.

38 Claims, 10 Drawing Sheets

CONTROL SYSTEM FOR ATOMIZING LIQUIDS WITH A PIEZOELECTRIC VIBRATOR

CROSS REFERENCE TO RELATED APPLICATIONS

This is a Continuation-in-Part of Provisional Application No. 60/124,155 filed Mar. 5, 1999.

BACKGROUND OF THE INVENTION

1. Field of the Invention

This invention relates to the atomization of liquids by means of a piezoelectric vibrator and more specifically it concerns novel methods and apparatus for controlling such atomization in an efficient and effective manner.

The present invention also relates to means for the distribution of a liquid active material, such as a perfume, air freshener, insecticide formulation, or other material, in the form of fine particles or droplets, as in a fine spray, by means of a piezoelectric device. In particular, the invention is directed to a piezoelectric liquid delivery system for production of droplets of liquid, or liquid suspensions, by means of an electromechanical or electroacoustical actuator. Even more specifically, the present invention relates to an improved control circuit for use with such devices.

2. Description of the Related Art

The use of piezoelectric vibrators to atomize liquids is well known; and examples of such devices are described in U.S. Pat. No. 5,164,740, U.S. Pat. No. 4,632,311 and U.S. Pat. No. 4,533,082. In general, these devices apply an alternating voltage to a piezoelectric element to cause it to expand and contract. The piezoelectric element is coupled to a perforated orifice plate, which in turn is in contact with a liquid source. The expansion and contraction of the piezoelectric element causes the orifice plate to vibrate up and down whereupon liquid is driven through the orifice plate's perforations and is then thrown upwardly in the form of fine aerosolized particles.

It is desired to provide a battery driven piezoelectric atomizer which operates over a long period of time without deterioration of its performance and which permits the use of inexpensive alkaline batteries whose voltage output is known to decrease over the operating life of the battery.

One way in which a piezoelectric atomizer can be driven economically is to control it to operate during drive periods which are separated by sleep periods, so that liquid becomes atomized during the drive periods in successive short puffs. However, during the sleep periods between puffs, liquid accumulates on the orifice plate; and in order to start a successive puff at the next drive period, the orifice plate must be driven at a large amplitude.

Another way in which a battery operated piezoelectric atomizer can be operated economically is to drive it at the resonant frequency of its vibrating system, which includes the orifice plate, the piezoelectric element and any mechanical coupling between the orifice plate and the element. A problem occurs, however, because the resonant frequency may vary somewhat from device to device so that a different driving frequency must be set for each unit.

The distribution of liquids by formation of a fine spray, or atomization, is well known. One method for such distribution is to atomize a liquid by means of the acoustic vibration generated by an ultrasonic piezoelectric vibrator. An example of such a method is shown in U.S. Pat. No. 4,702,418, which discloses an aerosol dispenser including a nozzle chamber for holding fluid to be dispensed and a diaphragm forming at least a portion of the chamber. An aerosol dispensing nozzle is disposed therein, with a restrictive passage for introducing liquid from the reservoir to the nozzle. A pulse generator in combination with a low voltage power source is used to drive a piezoelectric bender, which drives fluid from the reservoir through the nozzle to create an aerosol spray.

Another atomizer spraying device is shown in U.S. Pat. No. 5,518,179, which teaches a, liquid droplet production apparatus comprising an orifice plate which is vibrated by an actuator which has a composite thin-walled structure, and is arranged to operate in a bending mode. Liquid is supplied directly to a surface of the orifice plate and sprayed therefrom in fine droplets upon vibration of the orifice plate.

U.S. Pat. Nos. 5,297,734 and 5,657,926 teach ultrasonic atomizing devices comprising piezoelectric vibrators with a vibrating plate connected thereto.

In U.S. Pat. No. 5,297,734, the vibrating plate is described as having a large number of minute holes therein for passage of the liquid.

While a number of additional patents disclose means for the dispersion of liquids by ultrasonic atomization, or for timed intervals of dispersion, they have achieved only moderate success in the efficient atomization of such materials as perfumes. See, e.g., U.S. Pat. Nos. 3,543,122, 3,615,041, 4,479,609, 4,533,082, and 4,790,479. The disclosures of these patents, and of all other publications referred to herein, are incorporated by reference as if fully set forth herein.

Such atomizers fail to provide an easily portable, battery operated dispenser employing an orifice plate in mechanical connection with a piezoelectric element, capable of long periods of use with little or no variation in the delivery rate. Furthermore, the efficiency of these atomizers may differ due to manufacturing differences in the atomizer piezoelectric pump components. Thus, a need exists for improved atomizers or dispensers for use in distribution of active fluids such as fragrances and insecticides, which atomizers are highly efficient and consume minimal electrical power while providing wide dispersal of the liquid.

SUMMARY OF THE INVENTION

The present invention in is various aspects, overcomes the above problems.

In one aspect, the present invention involves a novel method for operating a vibratory liquid atomizer of the type in which an orifice plate, to which liquid to be atomized is supplied, vibrates to drive the liquid from its surface in the form of fine aerosolized liquid particles. This novel method includes the steps of initially vibrating the orifice plate at a relatively high amplitude to initiate atomization of the liquid: and thereafter vibrating the orifice plate at a relatively lower amplitude sufficient to sustain the atomization.

In another aspect, the invention involves a novel method for operating a piezoelectric vibratory liquid atomizer of the type in which a piezoelectric actuating element is energized by an alternating voltage to expand and contract and thereby to vibrate an orifice plate, to which a liquid to be atomized is supplied, so that the vibration of the orifice plate atomizes said liquid and ejects it from the orifice plate in the form of fine aerosolized particles. This novel method comprises the steps of first applying a relatively high alternating voltage to said the piezoelectric actuating element to cause it to vibrate the orifice plate at a high amplitude to initiate atomization of the liquid; and thereafter applying a relatively lower alternating voltage to the piezoelectric actuating element to sustain atomization.

In a further aspect the invention involves a novel vibratory liquid atomizer which comprises an orifice plate, a liquid conduit which is arranged to supply liquid to be atomized to the orifice plate, and a vibration actuator connected to first vibrate the orifice plate during a drive period at a relatively high amplitude to initiate atomization of the liquid and thereafter, during the same drive period, to vibrate the orifice plate at a relatively lower amplitude sufficient to sustain the atomization.

In a still further aspect, the present invention involves a novel vibratory liquid atomizer which comprises an orifice plate mounted which is mounted to be vibrated, a liquid supply conduit arranged to supply liquid to the orifice plate while it is vibrating, a piezoelectric actuating element coupled to the orifice plate to cause it to vibrate when the piezoelectric element expands and contracts, and an electric power supply system connected to supply an alternating voltage to the actuating element during a drive period to cause it to expand and contract and thereby to vibrate the orifice plate to atomize the liquid and eject it in the form of fine aerosolized liquid particles. The electric power supply system includes circuits which are connected to first apply a high alternating voltage to said the piezoelectric actuating-element to cause it to vibrate the orifice plate at a relatively high amplitude to initiate atomization of the liquid and thereafter to apply a relatively lower alternating voltage to the piezoelectric actuating element to sustain atomization.

A primary purpose of the present invention is to provide, a highly efficient method for dispensing such liquids as perfumes, air fresheners, or other liquids. Such other liquids include household cleaning materials, sanitizers, disinfectants, repellants, insecticides, aroma therapy formulations, medicinals, therapeutic liquids, or other liquids or liquid suspensions which benefit from atomization for use. These compositions may be aqueous, or comprise various solvents.

It is an object of the present invention to provide improved control circuits for use with an easily portable, battery operated dispenser employing a domed orifice plate in mechanical connection with a piezoelectric element. The piezoelectric pump is capable of operating efficiently for months, on low voltage batteries, while maintaining consistency of delivery throughout the period. A piezoelectric atomizer is capable for use with such electrical sources as 9 volt batteries, conventional dry cells such as "A", "AA", "AAA", "C", and "D" cells, button cells, watch batteries, and solar cells. The preferred energy sources for utilization in combination with the present invention are "AA" and "AAA" cells.

The piezoelectric pump has circuitry to compensate for manufacturing differences in the pump components. The electronics of such circuitry may be programmable, and may be used to set a precise delivery rate (in milligrams per hour, hereinafter mg/hr). Alternatively, the electronic circuitry may allow the consumer to adjust intensity or effectiveness to a desired level for personal preference, efficacy, or for room size.

In the preferred embodiment of the present invention, these and other objects of this invention are achieved by an atomizer for fragrances, insecticide formulations, and other liquids such as set forth previously, wherein the atomization system includes a chamber for the liquid to be dispensed, means to supply the liquid from said chamber to an orifice plate for dispersal of the liquid, a piezoelectric element, an energy source, and the improved circuitry to drive and control the piezoelectric element. It has been found that by controlling the amplitude and frequency of the signal driving the piezoelectric element, superior results are attained. The present invention thus provides a means for more uniform atomization of the liquid to be dispensed throughout the total period of dispersion, such that the amount dispersed per time unit at the commencement of dispersion does not vary as greatly from the amount dispersed near or at the finish of dispersion. These and still other objects and advantages of the present invention will be apparent from the description which follows, which is, however, merely of the preferred embodiments. Thus, the claims should be looked to in order to understand the full scope of the invention.

The invention also involves other specific features which are described hereinafter; and which in combination with the foregoing features, provide additional advantages.

DETAILED DESCRIPTION OF THE PREFERRED EMBODIMENTS

Figure 1:
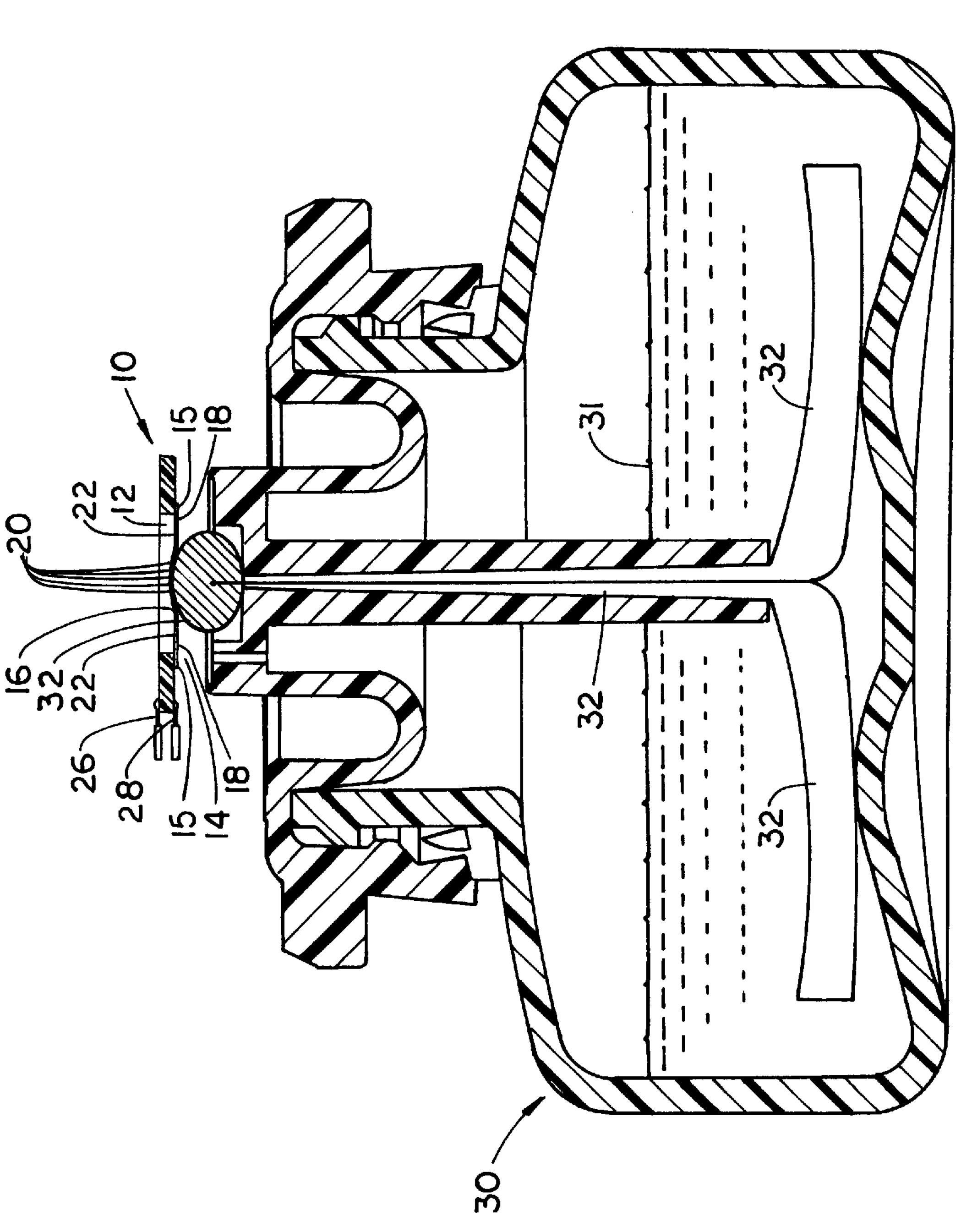
FIG. 1 is a sectional elevation view of an atomizing device with the invention may be used.

FIG. 1 shows a vibratory atomizing device which may be operated according to the present invention. This device comprises an annularly shaped piezoelectric actuator 10 having a center hole 12 and a circular orifice plate 14 which extends across the hole 12 on the underside of the actuator and slightly overlaps an inner region 15 of the actuator. The orifice plate 14 is fixed to the underside of the actuator 10 in the overlap region 15. Any suitable cementing means may be used to fix the member 14 to the piezoelectric element 10; however, in cases where the device may be used to atomize liquids which are corrosive or aggressive in that they tend to dissolve or soften the material which binds the orifice plate to the piezoelectric actuator, it is preferred that the orifice plate be soldered to the piezoelectric element by means of a tin-lead or silver solder.

The piezoelectric actuator 10 may be made from any material having piezoelectric properties which cause it to change dimensionally in a direction perpendicular to the direction of an applied electric field. Thus in the illustrated embodiment, the piezoelectric actuator 10 should expand or contract in a radial direction when an electrical field is applied across its upper and lower surfaces. The piezoelectric actuator 10 may, for example, be a ceramic material made from a lead zirconate titanate (PZT) or lead metaniobate (PN). In the embodiment illustrated herein, the piezoelectric actuator has an outer diameter of about 0.382 inches and a thickness of about 0.025 inches. The diameter of the center hole 12 is about 0.177 inches. These dimensions are not critical and they are given only by way of example.

The orifice plate 14 in the illustrated embodiment is about 0.250 inches in diameter and has a thickness of about 0.002 inches. The orifice plate 14 is formed with a slightly domed center region 16 and a surrounding flexible flange region 18 which extends between the domed center region 16 and the region where the orifice plate is affixed to the actuator 10. The domed center region 16 has a diameter of about 0.103 inches and it extends out of the plane of the orifice plate by about 0.0065 inches. The domed center region contains several (for example 85) small perforations 20 which have a diameter of about 0.000236 inches and which are spaced from each other by about 0.005 inches. A pair of diametrically opposed holes 22 are formed in the flange region 18. These holes have a diameter of about 0.029 inches.

Again, these dimensions are not critical and only serve to illustrate a particular embodiment.

It will be noted that the doming of the center region 16, which contains the perforations 20, makes this region stiff so that it does not bend during actuation, whereas the flange region 18, which contains the holes 22, remains flexible so that it does bend during actuation. While the domed center region is spherical in configuration, any configuration which will maintain stiffness in this region may be used. For example, the center region 16 may have a parabolic or arcuate shape.

The orifice plate 14 is preferably made by electroforming with the perforations 20 and the holes 22 being formed in the electroforming process. However, the orifice plate may be made by other processes such as rolling; and the perforations and holes may be formed separately. For ease in manufacture, the center region 16 is domed after the perforations 18 have been formed in the orifice plate.

The orifice plate 14 is preferably made of nickel, although other materials may be used, provided that they have sufficient strength and flexibility to maintain the shape of the orifice plate while being subjected to flexing forces. Some examples of alloys that could be used are nickel-cobalt and nickel-palladium alloys.

The piezoelectric actuator 10 may be supported in any suitable way which will hold it in a given position and yet not interfere with its vibration. Thus, the actuator may be supported in a grommet type mounting (not shown). The coatings may be formed from other electrically conductive materials, including, for example, silver and nickel.

The piezoelectric element 10 is coated on its upper and lower surfaces with an electrically conductive coating such as aluminum. As shown, electrical leads 26 and 28 are soldered to the electrically conductive coatings on the upper and lower surfaces of the actuator 10. These leads extend from a source of alternating voltages (not shown).

A liquid reservoir 30, which contains a liquid 31 to be atomized, is mounted below the actuator 10 and orifice plate 14. A wick 32 extends up from within the reservoir to the underside of the orifice plate 14 so that it lightly touches the orifice plate in the center region 16 and so that it contacts the perforations 20. However, the wick should not touch the holes 22 and these holes should be laterally displaced from the wick. The wick 32 may be made of a porous flexible material which provides good capillary action to the liquid in the reservoir 30 so as to cause the liquid to be pulled up to the underside of the orifice plate 14. At the same time the wick should be sufficiently flexible that it does not exert pressure against the orifice plate which would interfere with its vibratory motion. Subject to these conditions, the wick 32 may be made of any of several materials, for example, paper, nylon, cotton, polypropylene, fiberglass, etc. A preferred form of wick 30 is nylon chenille yarn that is bent back on itself where it touches the orifice plate. This causes very thin fibers of the strand to extend up to the orifice plate surface. These very thin fibers are capable of producing capillary action so as to bring liquid up to the orifice plate; however, these thin fibers do not exert any appreciable force on the orifice plate which would interfere with its vibratory movement.

In operation of the atomizer, alternating electrical voltages from an external source are applied through the leads 26 and 28 to the electrically conductive coatings on the upper and lower surfaces of the actuator 10. This produces a piezoelectric effect in the actuator material whereby the actuator expands and contracts in radial directions. As a result, the diameter of the center hole 12 increases and decreases in accordance with these alternating voltages. These changes in diameter are applied as radial forces on the orifice plate 14; and as a result, the flange region 18 flexes and pushes the domed center region 16 up and down. This produces a pumping action on the liquid which is brought up against the underside of the center region 16 by the wick 32. The capillary action of the wick causes the pressure of the liquid on the underside of the orifice plate 14 to be slightly higher than the atmospheric pressure above the orifice plate. As a result, the liquid 31 is forced upwardly through the perforations 20 and is ejected from the upper surface of the orifice plate as fine aerosolized liquid particles into the atmosphere.

Figure 2:
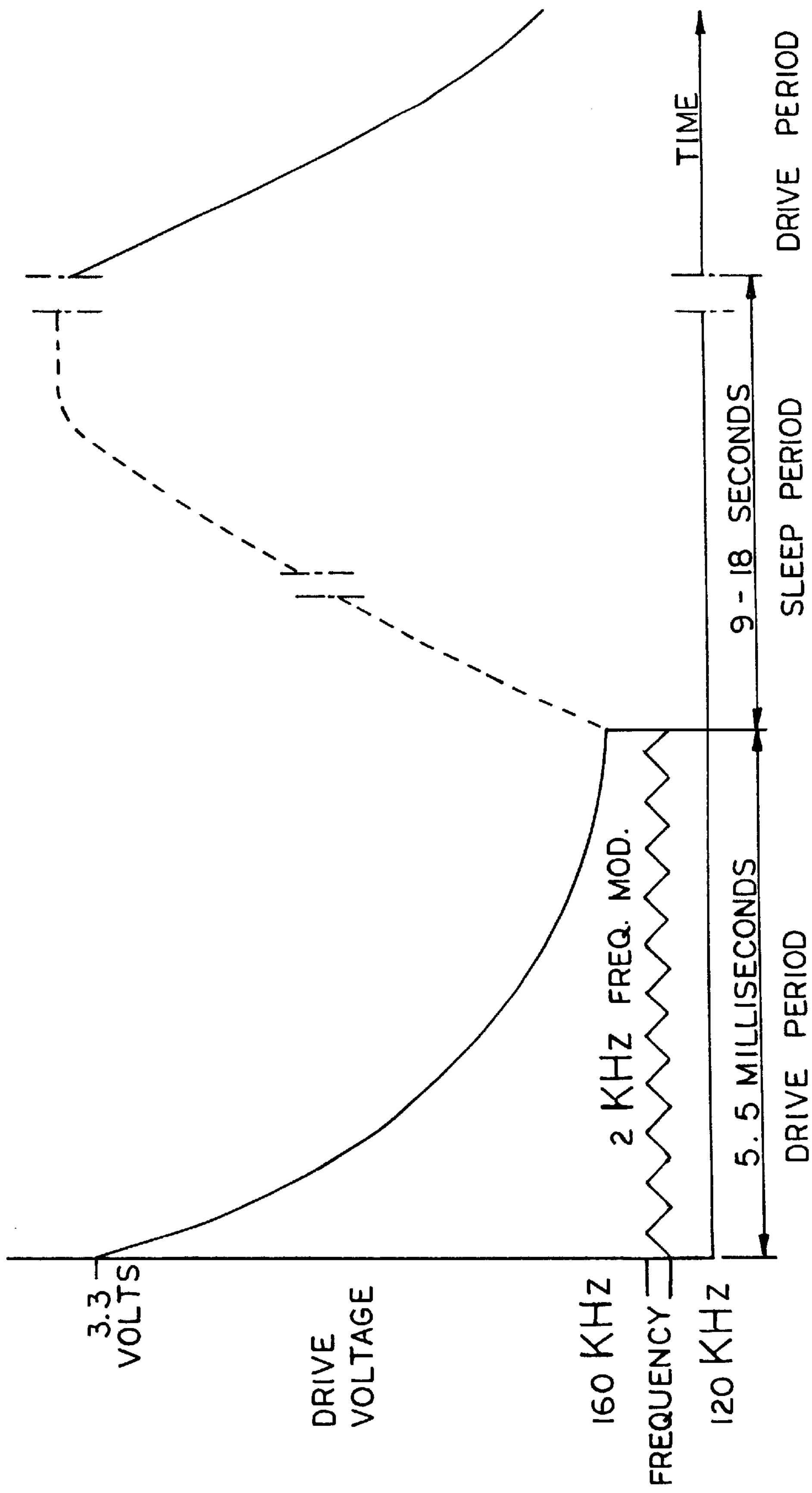
FIG. 2 is a timing diagram showing the operation of the device of FIG. 1 according to the invention.

FIG. 2 shows the driving sequence of the piezoelectric actuation element 10 according to the invention. As shown in FIG. 2, the driving sequence is divided into alternate drive periods of 5.5 milliseconds duration, and sleep periods of from 9 to 18 seconds duration.

During the 5.5 millisecond drive periods, the voltage used for driving the piezoelectric actuation element 10 decreases exponentially from 3.3 volts down to about 1 volt. Thus the piezoelectric actuating element 10 is initially driven at a high amplitude, which clears liquid from its surface and initiates atomization; and then it is driven at significantly lower amplitudes, which are sufficient to maintain actuation but which consume only minimal amounts of driving power. It should be understood that the invention is not limited to one cycle of high and low amplitude driving during a particular drive period, but in fact the high and low amplitude sequence may be repeated any number of times that may be necessary to sustain atomization.

After each drive period, the system goes into a sleep period of from 9 to 18 seconds. During the first 4 seconds of each sleep period the system recharges back to 3.3 volts and this voltage is maintained for use during the next drive period. It should also be understood that, for some applications, the succession of high and low amplitude drive could be repeated continuously without any intervening sleep periods.

It will be noted that the actuation element 10 is capable of driving the orifice plate 14 at a sufficient amplitude to atomize the liquid 31 when the element 10 is driven from a supply voltage source of only 1.5 volts; however in order to initiate atomization, the element 10 must be driven using a higher supply source voltage, such as 3.3 volts, in order to vibrate the orifice plate 14 at a sufficient amplitude to clear a film of liquid which had accumulated on its outer surface during the previous sleep period. Thus the orifice plate 14 is initially driven at high power to produce high amplitude vibrations which initiate atomization; but once atomization has begun, a much lower vibrational amplitude may be used to sustain atomization. By having the driving voltage decrease from 3.3 volts to 1 volt at an exponential rate, the total energy expended is reduced and battery life can thereby be extended significantly.

At the end of each 5.5 millisecond drive period, the system enters a "sleep period" of from 9 to 18 seconds. The length of this sleep period can be set at 9 seconds, 13.5 seconds or 18 seconds by means of a selector switch as described hereinafter.

The first 4 seconds of each sleep period is used for recharging the supply for driving the system back from 1 volt to 3.3 volts. Thus when the next successive drive period begins, the orifice plate 14 will initially be driven at a high amplitude from a 3.3 volt drive voltage supply.

The vibratory amplitude of the orifice plate 14 depends not only on the voltage used for producing the vibrations, it also depends on the frequency used to drive the orifice plate. This is because the vibratory system which includes the orifice plate 14, the piezoelectric driving actuator 10, and any interconnections between these members, has a natural resonant frequency. When this system is driven at its natural resonance frequency, the vibrational amplitude of the orifice plate is maximized, while the driving power is minimized. However, because of tolerances of manufacture, the resonant frequency of the orifice plate and actuator system differs from device to device.

In order to solve this problem, the driving frequency is varied or swept over a range which includes a harmonic of the resonant frequency of the orifice plate and actuator system. Thus, the driving frequency should sweep over a range which includes the base natural resonant frequency (first harmonic) or over a range which includes some higher harmonic of the natural resonant frequency of the orifice plate and actuator system. Thus, even though the specific resonant frequency of a particular system is not known, by driving it through a range of frequencies, it will be caused to resonate at some point in this frequency range. As shown in FIG. 2, the drive frequency is swept over a predetermined frequency range of from 120 to 160 kilohertz. The frequency range is swept back and forth at least eleven times during each 5.5 millisecond drive period. As previously explained in connection with the drive amplitudes, the frequency sweep may also be carried out continuously without intervening sleep periods.

Figure 3:
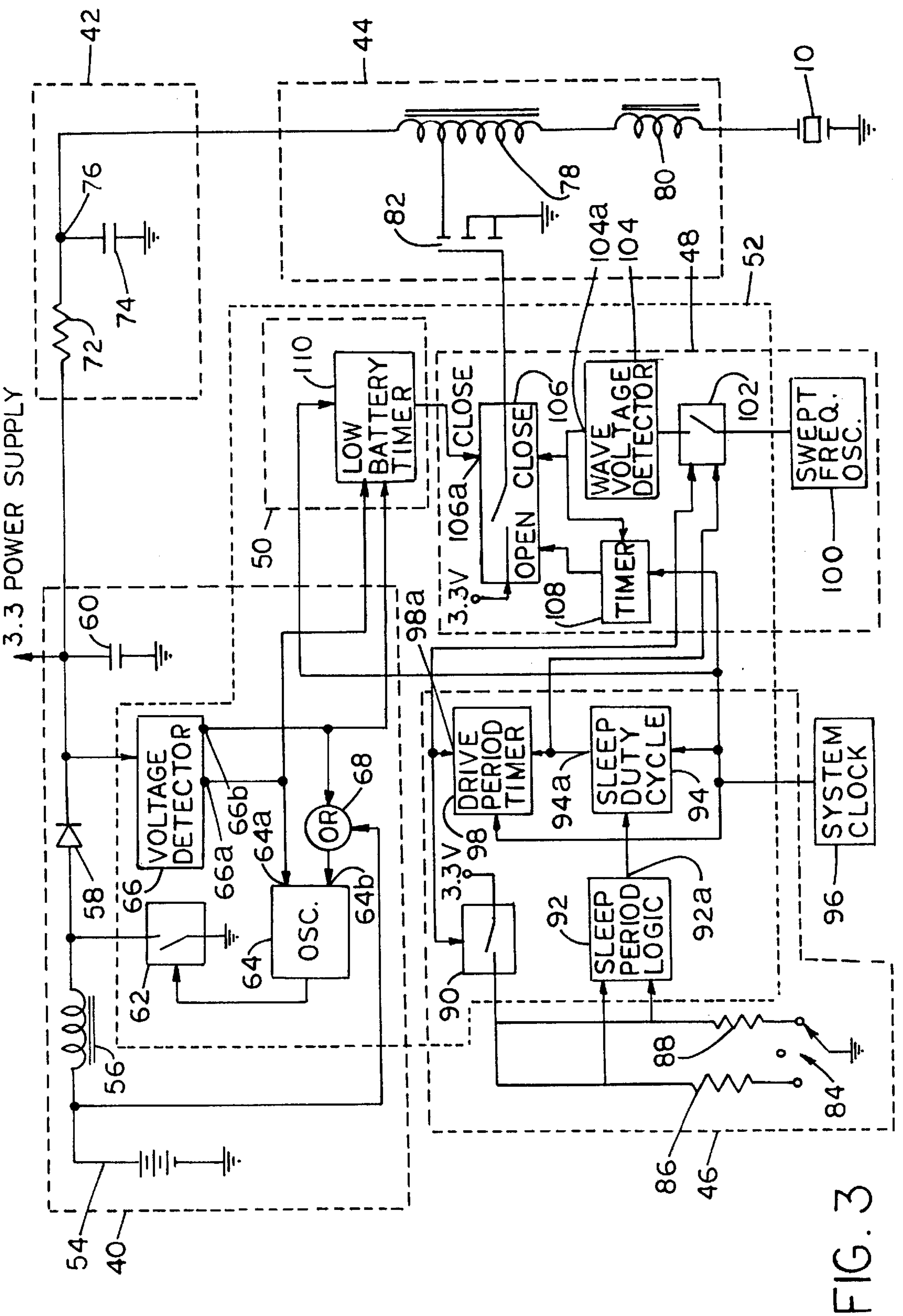
FIG. 3 is a simplified block diagram showing the arrangement of elements of a control system according to the present invention.

FIG. 3 is a simplified block diagram for explaining a circuit arrangement that may be used for driving the piezoelectric actuator element 10 according to the invention. For purposes of explanation, this circuit arrangement is described as a group of functional units which are shown in dashed outline. These functional units are as follows:

(a) an operating power supply unit 40;

(b) a drive voltage pattern control unit 42;

(c) a drive signal amplification unit 44;

(d) the piezoelectric actuator element 10;

(e) a sleep period control unit 46;

(f) a frequency pattern control unit 48; and (g) a low battery detection and control unit 50.

Portions of each of these units are formed in a common integrated circuit 52 (shown in dotted outline) while other portions are mounted on a printed circuit board (not shown) together with the integrated circuit 52, as will be described more fully hereinafter.

The operation of the circuit arrangement of FIG. 3 will first be described in regard to the overall operation of the functional units 40, 42, 44, 46, 48 and 50; and thereafter the individual operation of each functional unit will be described.

Overall Description of the Functional Units

The operating power supply unit 40 converts the voltage output of a 1.5 volt "AA" alkaline battery 54 to a 3.3 volt operating voltage. The 3.3 volt operating voltage is used to power the other circuits in the system, including the drive voltage pattern control unit 42.

The drive voltage pattern control unit 42 causes the operating voltage to follow a generally exponential decrease from 3.3 volts to 1 volt during the successive 5.5 millisecond drive periods shown in FIG. 2. Here it should be noted that an exponential decrease is not critical to this invention. Actually once atomization is initiated at the beginning of each drive period, the voltage can be lowered as rapidly as possible in order to conserve battery power, so long as the atomization function is sustained.

The voltage from the drive voltage pattern control unit 42 is supplied to the drive signal amplification control unit 44 where it is amplified and converted into a swept frequency voltage output which is used to energize the piezoelectric actuator element 10.

The sleep period control unit 46 controls the duration of the sleep periods indicated in FIG. 2. In the illustrated embodiment, these sleep periods can be set for durations of either 9, 13.5 or 18 seconds. The sleep periods may be set for other durations, provided that they are long enough to allow the operating power supply unit 40 to bring the drive voltage pattern control unit 42 back to its 3.3 volt level for the next drive period. In the present embodiment, the recharging to 3.3 volts requires about 4.5 seconds.

The frequency pattern control unit 48 produces an alternating voltage signal having a frequency which is swept between 120 and 160 kilohertz. This signal is applied to the drive signal amplification and frequency control unit 44 which in turn drives the piezoelectric actuator 10 at these frequencies and at a decreasing amplitude corresponding to the drive period voltage pattern set by the drive voltage pattern control 42.

The low battery detection and control unit 50 senses the voltage output of the battery 54; and when this voltage output decreases to a predetermined level at which the battery no longer operates reliably, the detection and control unit 50 prevents further operation of the system. At the same time, the unit 50 causes the battery 54 to drain to a level such that it cannot recover sufficient output voltage to cause inadvertent sporadic operation of the atomizer device.

The Operating Power Supply Unit

The operating power supply unit 40 includes, in addition to the battery 54, a pumping coil 56, a Zener diode 58 and a storage capacitor 60. The battery 54 is connected between ground at its cathode and one end of the pumping coil 56.

The other end of the coil 56 is connected to the anode of the Zener diode 58, while the diode's cathode is connected to one side of the storage capacitor 60. The other side of the capacitor 60 is connected to ground. A voltage controlled switch 62 has one side connected between the coil 56 and the diode 58, while the other side of the switch 62 is connected to ground. The switch 62 is alternately opened and closed at a 200 kilohertz rate by the output of a 200 kilohertz pumping oscillator 64. A voltage detector 66 is connected to sense the voltage at a point between the Zener diode 58 and the storage capacitor 60. The voltage detector 66 has a high sensed voltage output terminal 66*a* and a low sensed voltage output terminal 66*b*. These output terminals are connected to stop and start inputs 64*a* and 64*b*, respectively, of the pumping oscillator 64.

The start input 64*b* of the pumping oscillator 64 is also connected to receive directly the 1.5 volts output of the battery 54. Thus the voltage detector low sensed voltage terminal 66*b* and the battery 54 output are shown to be connected to the start terminal of the pumping oscillator 64 via an OR gate 68.

When the battery 54 is first installed, its 1.5 volt output is supplied through the OR gate 68 to the start input terminal of the pumping oscillator 64 to start operation of the oscillator. The oscillator output causes the switch 62 to open and close at a 200 kilohertz rate. When the switch is closed, current from the battery 54 flows through the pumping coil 56 to ground. Then, when the switch 62 closes, the flow of current is suddenly interrupted and the inductance of the pumping coil causes it to experience a sudden rise in voltage, which allows current to pass through the zener diode 58 and into the storage capacitor 60. When the switch 62 opens again the voltage of the pumping coil decreases, but because of the diode effect, current cannot flow back through the coil 56. As the oscillator 64 continues to operate, the voltage on the storage capacitor 60 increases until it reaches about 3.3 volts.

The voltage on the storage capacitor 60 is detected by the voltage detector 66 which, when the voltage becomes just above 3.3 volts, produces a signal at its high sensed voltage output terminal 66*a*. This signal is supplied to the stop terminal 64*a* of the oscillator 64 causing it to stop oscillating, with the switch 62 in its open condition. As a result as current is drained from the storage capacitor, its voltage decreases until it reaches a point where the voltage detector 66 produces a signal at its low sensed voltage terminal 66*b*.

The low sensed voltage is applied to the start terminal 64*a* of the oscillator 64 which causes the switching action of the switch 62 to resume and to begin further pumping of current into the storage capacitor 60.

It will be seen that the voltage at the capacitor 60 is thus caused to dither between slightly above and slightly below 3.3 volts depending on the high and low voltage settings of the voltage detector 66. The 3.3 volts on the capacitor 60 is supplied to operate the remaining components, as represented by the output power supply terminal 70.

The Drive Voltage Pattern Control Unit

The drive voltage pattern control unit 42 comprises a resistor 72 connected at one end to the storage capacitor 60 in the operating power supply unit 40. The other end of the resistor 72 is connected to one side of a voltage pattern control capacitor 74. The other side of this capacitor is connected to ground. The resistor 72 and the capacitor 74 form a standard RC timing circuit; and the voltage at a junction 76 between the resistor and capacitor decreases at an exponential rate when it is connected to a finite impedance. In the present embodiment, the voltage at the junction 76 decreases from 3.3 to about 1 volt in about 5.5 milliseconds.

The Drive Signal Amplification Unit

The drive signal amplification unit 44 comprises an autotransformer 78 and a smoothing coil 80 connected in series between the junction 76 in the drive voltage pattern control unit 42 and one side of the piezoelectric actuator element 10. Also, there is provided a field effect transistor 82 which is connected between a point 78*a* along the autotransformer 78 and ground. The field effect transistor 82 acts as a switch, and when it receives a positive voltage from the frequency pattern control unit 48, it becomes conductive and connects the point 78*a* to ground.

Point 78*a* is located near the upper end of the autotransformer 78 closest to the drive voltage pattern control unit 42 such that only a minor portion of the autotransformer's coils are between the point 78*a* and the drive voltage pattern control unit 42. When the point 78*a* becomes disconnected from ground, the autotransformer effect produces a very high voltage at its end closest to the actuation element 10 and causes the element to expand and contract. The voltage signal from the autotransformer first passes through the smoothing coil 80 to convert it to a pattern corresponding more closely to that of the oscillation pattern of the actuator element 10.

The Sleep Period Control Unit

The sleep period control unit 46 comprises a three position selector switch 84 whose common terminal is connected to ground and two of whose three switch terminals are connected through time control resistors 86 and 88 to a sampling switch 90. The switch 90 in turn is connected to the 3.3 volt supply voltage. The third switch terminal is not connected.

The resistors 86 and 88 are also connected to supply different voltages to a sleep period logic circuit 92, depending on the particular switch terminal that is connected to ground. The logic circuit 92 compares the voltages which it receives from the resistors 86 and 88; and it outputs one of three different voltages at an output terminal 92*a*. This voltage is supplied to a sleep duty cycle circuit 94 which acts as a timer to produce an output at an output terminal 94*a* at either 9, 13.5 or 18 seconds after receiving a signal from the logic circuit 92.

There is provided a system timing clock 96 which provides clock signals at a 2 kilocycle rate. These clock signals are used for all of the timing circuits and table reading circuits in the device, including the duty cycle circuit 94.

When the duty cycle circuit 94 reaches the 9, 13.5 or 18 second interval to which it has been set, it produces a signal at an output terminal 94*a* which is supplied to the frequency pattern control unit 48 to initiate driving of the piezoelectric actuation element 10. The manner in which this is done is explained hereinafter in connection with the description of description of the frequency pattern control unit 48.

The signal at the output terminal 94*a* of the sleep duty cycle circuit is also applied to a drive timer 98 which sets the driving time period for the piezoelectric actuator element 10. In the illustrative example, this driving time period is 5.5 milliseconds. At the end of this period, the drive timer 98 outputs a signal from an output terminal 98*a*. This signal is transmitted to the frequency pattern control unit 48 to discontinue driving of the piezoelectric actuator element 10.

The signal from the output 98*a* of the drive timer is also transmitted to the sampling switch 90 to cause it to close momentarily. This causes a voltage drop to occur across the resistor 86 or 88 which has been selected by the setting of the selector switch 84. If the selector switch is set to its unconnected terminal, no voltage drop will occur. Thus, either a zero voltage, a first voltage, or a second voltage is produced each time the sample switch 90 is closed. This voltage is applied to the sleep time select logic unit 92 to initiate a sleep time duration corresponding to the position of the sleep selector switch 84. Thus at the end of each drive period of the piezoelectric actuator element 10, a new sleep period is initiated; and the length of this sleep period depends on the position of the selector switch at the time the sleep period begins.

The Frequency Pattern Control Unit

The frequency pattern control unit 48 includes a swept frequency oscillator 100, which in the present example, produces a triangular waveform output at a frequency which sweeps between 130 and 160 kilohertz. This output is applied to a drive period on and off switch 102. The switch 102 is connected to be closed by a signal from the output terminal 94*a* of the sleep duty cycle circuit 94, and to be opened by a signal from the output terminal 98*a* of the drive timer 98. Thus, the variable frequency outputs from the oscillator 100 pass through the drive period on and off switch 102 only during the 5.5 millisecond drive periods for the piezoelectric actuator 10.

The variable frequency outputs which pass through the switch 102 are applied to a wave voltage threshold detector 104. This device produces an output signal at an output terminal 104*a* at a particular point in each output cycle from the swept frequency oscillator 100, namely the point in each cycle when the output voltage from the oscillator reaches a predetermined threshold.

This output signal from the wave voltage threshold detector 104 is applied to a driver switch 106 to cause it to close. The driver switch 106, when closed, connects a positive voltage, such as the 3.3 volt power supply, to the gate terminal of the field effect transistor 82 to make it conductive.

The signal from the output of the voltage threshold detector 104 is also supplied to a wave segment control timer 108. This timer produces an output signal after a fixed duration, less than the duration of one cycle of the swept frequency oscillator 100.

The output signal from the timer 108 is applied to the driver switch 106 and causes it to open. The opening of the driver switch 106 causes the field effect transistor 82 to become non-conductive so that current may no longer flow from the upper portion of the autotransformer 78 to ground. During this time the autotransformer causes a very large voltage to be imposed on the piezoelectric actuator 10.

It will be seen from the foregoing, that during each output cycle of the swept frequency oscillator 100, the drive control switch 106 is closed for a fixed duration to produce a fixed amount of energy to cause the driving of the piezoelectric actuator element 10. At the same time, the spacing in time between successive ones of these fixed durations varies according to the frequency of the variable frequency oscillator 100. This fixed driving duration for each drive cycle permits the piezoelectric actuator 10 to be driven at a variable frequency while keeping the driving energy independent of the frequency. Thus the driving energy or amplitude of driving of the piezoelectric actuator 10 is made solely dependent on the voltage at any particular time at the junction 76 between the capacitor 74 and the resistor 72 in the drive voltage pattern control unit 42. As a result, during each drive period, the piezoelectric actuator 10 is driven at a varying frequency at a decreasing amplitude. It will be appreciated that this frequency is swept between 130 and 160 kilohertz approximately 11 times during each driving period, while the driving amplitude decreases once.

The Low Battery Detection and Control Unit

The low battery detection and control unit 50 operates to maintain the system in operation for so long as the battery 54 is capable of having its voltage pumped to a 3.3 volt level within a predetermined duration, namely within the first 4 seconds of each sleep period. The unit 50 comprises a low battery timer 110 which is connected to receive a start timing input signal from the low voltage output terminal 66*b* of the voltage detection circuit 66 in the operating power supply unit 40, and to receive a stop timing signal from the high voltage output terminal 66*a* of the voltage detection circuit 66. Thus whenever an operation is initiated to begin pumping the supply voltage to 3.3 volts, the timing operation of the low battery timer 110 is initiated.

If the pumping action is completed within the duration set for the timer, for example 4 seconds, the signal from the high voltage terminal of the voltage detector 66 will stop timing action. If however, the pumping action continues for a longer duration, which occurs when the battery condition has deteriorated, the low battery timer 110 will produce a signal at an output terminal 110*a*.

The signal from the low battery timer 110*a* is applied to a close terminal 106*a* of the drive switch 106 to hold the switch closed. This locks the gate of the field effect transistor 82 to the 3.3 volt supply to hold the transistor in a conductive state. As a result, the voltage on the capacitors 60 and 74 is drained and current is drawn from the battery 54 through the field effect transistor 82 to ground. This action forcibly drains the remaining life out of the battery so that is prevented from sporadically operating the piezoelectric actuator 10 in the event it should recover a slight amount of voltage, as often happens when batteries wear down.

It will be appreciated that with the drive system of this invention, an inexpensive low voltage alkaline battery may be used to drive a piezoelectric actuator; and the operation of the actuator is maintained uniform even though the battery itself is wearing down. When the battery has deteriorated to a predetermined level, the device shuts off positively without having experienced any tailing off in its operation.

It is to be understood that the Figures, and the discussion herein, are directed to preferred embodiments of the invention, but that, the invention itself is broader than the illustrations given. Specifically, the invention is equally applicable to other forms of piezoelectric atomization, such as the use of cantilever beams and/or amplifying plates, as well as atomizers driven by conventional electric power, i.e. wall plug, rather than battery powered.

It will be appreciated that the specific circuit configurations shown herein are not critical to the invention and that possible modifications will readily be seen by those skilled in the art. The circuit arrangements shown herein are presented to most clearly illustrate and explain the important concepts of the present invention.

Figure 4:
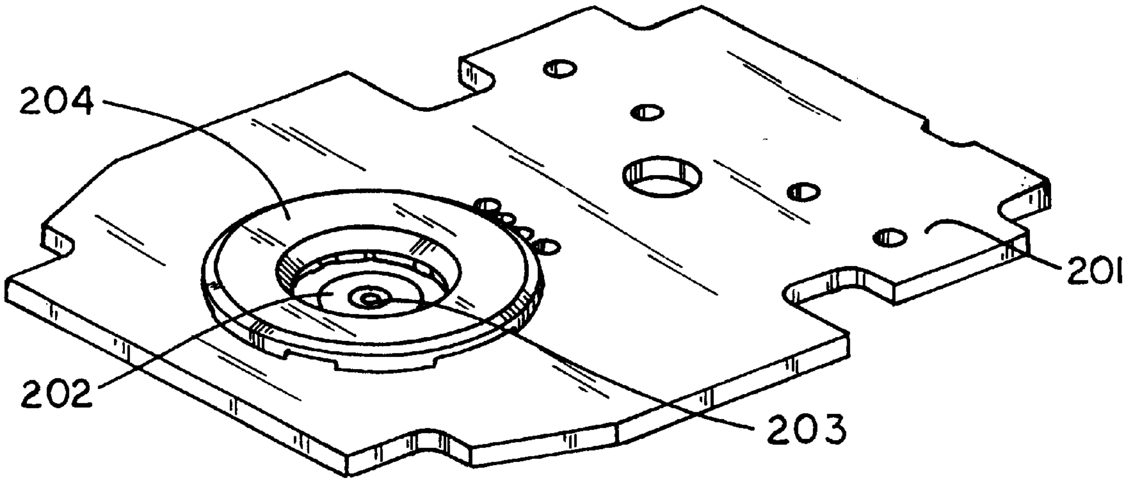
FIG. 4 is a partial isometric view of a circuit board suitable for use in a piezoelectric atomizer in accordance with a preferred embodiment of the present invention.
Figure 5:
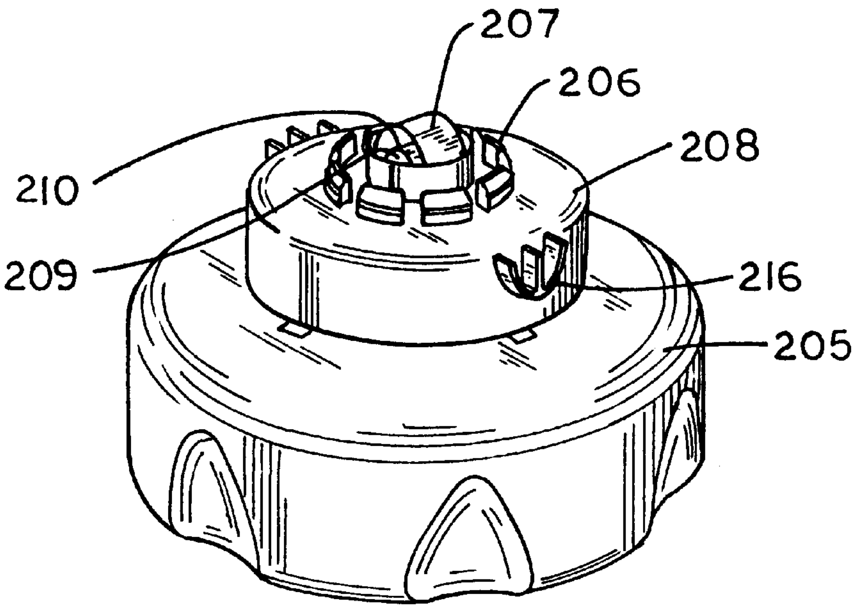
FIG. 5 is an isometric view of a liquid container and liquid transport means suitable to bring the liquid to the surface of the orifice plate.

FIG. 4 illustrates the general relationship between the printed circuit board, 201, and the piezoelectric element 202 located therein. It is to be understood that the circuit board may be, in use, attached to the chassis of the dispenser, which chassis may in turn be placed in a decorative shell-like housing or receptacle (not shown) for use. The chassis board 211 is shown in top view in FIG. 8, while the housing is not illustrated. The decorative receptacle or housing may be of any form or shape suitable for the purpose of retaining and protecting the elements of the dispenser while providing a pleasing appearance to the consumer, and permitting passage of the liquid, in spray form, from the dispenser to the atmosphere. As such, the dispenser housing may be advantageously produced by high speed molding of any material suitable for use with, and contact with, the liquid to be dispensed.

Piezoelectric element 202 may be mounted as illustrated in the circuit board 201, held in place by grommet 204, or by any similar suitable means which does not inhibit vibration of the element. The piezoelectric element 202, in the form of a ring, is positioned in an annular relationship to the orifice plate 203, and is attached to the orifice plate flange so as to be in vibratory communication therewith. The piezoelectric element generally comprises a piezoelectric ceramic material, such as a lead zirconate titanate (PZT) or lead metaniobate (PN), but may be any material exhibiting piezoelectric properties.

The orifice plate comprises any conventional material suitable for the purpose, but is preferably comprised of an electroplated nickel cobalt composition formed upon a photoresist substrate which is subsequently removed in conventional manner to leave a uniform porous structure of nickel cobalt having a thickness of from about 10 to about 100 microns, preferably from about 20 to about 80 microns, and most preferably about 50 microns. Other suitable materials for the orifice plate may be utilized, such as nickel, magnesium-zirconium alloy, various other metals, metal alloys, composites, or plastics, as well as combinations thereof. By forming the nickel cobalt layer through electroplating, a porous structure having the contour of the photoresist substrate may be produced, in which permeability is achieved by formation of conical holes having a diameter of about 6 microns on the exit side, and a larger diameter on the entrance side. The orifice plate is preferably dome shaped, i.e. somewhat elevated at the center, but may vary from flat to parabolic, arc shaped, or hemispherical in shape, or any other suitable shape which enhances performance. The plate should have a relatively high bending stiffness, to assure that the apertures therein still be subject to essentially the same amplitude of vibration, so as to simultaneously eject droplets of liquid which are uniform in diameter.

While shown in the form of an annular ceramic piezoelectric element surrounding an orifice plate or aperture, it is also conceived that the present invention is also suitable for use with a conventional piezoelectric element comprising an oscillator and a cantilever beam in contact with a diaphragm, nozzle, or orifice plate suitable for dispersion of liquid droplets or fog.

Also shown in FIG. 4 is the liquid container 205 for storage and provision of the fragrance, air freshener, insect control liquid, or other material to be dispensed. As illustrated, the container is closed by a closure 208. Also shown are bayonet clips 206, which are present to hold a removable top closure, or cap, not shown, which is used in transport and storage of the container, and may be removed easily when it is desired to put the container into the dispenser and permit use of the contents thereof. From bottle opening 209, exiting through the closure 208, projects the liquid supply means 207, a wick or dome shaped liquid feed medium. For convenience, we shall refer to the liquid supply means as a wick, although it may comprise a number of varying shape materials, from hard capillary systems to soft porous wicks. The function of the wick is to transport liquid from container 205 to a position in contact with the orifice plate. Accordingly, the wick should be unaffected by the liquid being transported, porous, and permit compliance with the orifice plate. The porosity of the wick should be sufficient to provide a uniform flow of liquid throughout the range of flexibility of the wick, and in any configuration thereof. To best transport the liquid to the surface of the orifice plate, it has been found necessary that the wick itself physically contact the plate to transfer the liquid to the orifice plate. Liquid is preferably delivered to the orifice plate in such a manner that essentially all delivered liquid will adhere to and transfer to the plate surface by surface tension. Among suitable wick materials, we have found it preferable to utilize such materials as paper, or fabrics of nylon, cotton, polypropylene, fiber glass, etc. The wick may preferably be shaped to conform to the surface of the orifice plate to which it is juxtaposed, and held in the correct position by a wick holder or positioner, 210, located in the bottle opening 209, of the closure 208 of liquid container 205. Liquid will flow readily from the wick to the plate as a result of the viscosity and surface tension of the liquid. It is to be noted that the wick is intended to be included as an integral part of a liquid resupply unit, which will comprise the container, the liquid, the bottle closure, the wick, and the wick holder or positioner, as well as a top closure to seal the unit for storage and shipment. Such a unit may thus comprise a refill bottle for the dispenser, suitable to be placed in the dispenser at the consumers convenience. To this end, the liquid container 205 may have attachment means 201 the bottle closure 208, for insertion into a suitable receiving means in the chassis 211 to lock it in operative position, after removal of the top closure or cap.

Figure 6:
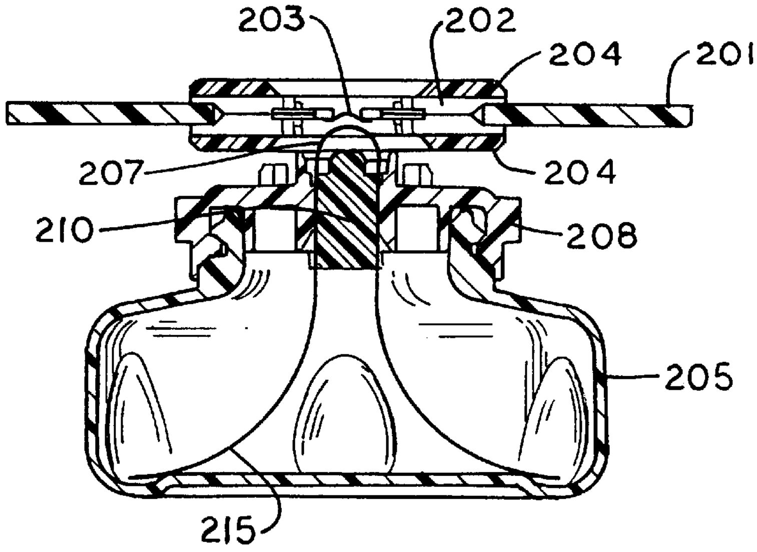
FIG. 6 is a cross sectional view showing the relationship of the liquid container, a feed means, and the piezoelectric element when assembled together.
Figure 7:
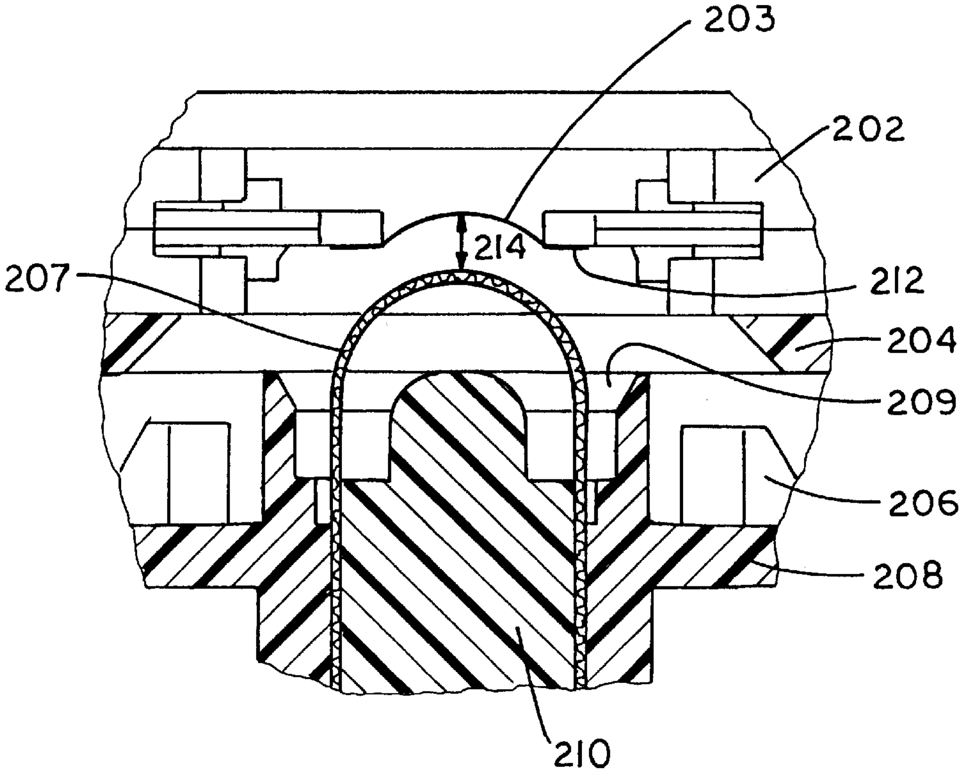
FIG. 7 is a magnified detail of the area of FIG. 6 enclosed within the circle.

FIG. 6 illustrates, in cross sectional view, the assembled relationship between the liquid container 205, the wick 207, the piezoelectric element 202, and the orifice plate 203 of a specific preferred embodiment of the invention. The piezoelectric element 202 is positioned, for example, in printed circuit board 201, by grommets 204, or by any suitable means which does not restrict vibration of the piezoelectric element. In a preferred embodiment of the invention, the annular piezoelectric element surrounds the orifice plate 203, in mechanical connection therewith. The orifice plate is, in turn, in contact with the wick 207, permitting the liquid to be dispensed from the container 205 to the orifice plate, where transfer occurs through surface tension contact. Not shown is the chassis ball of the dispenser, which holds the circuit board and the liquid container in the appropriate position to bring wick 207 into juxtaposition with the orifice plate 203. Wick 207 is held in the opening of closure 8 by the wick holder 210, which permits a degree of freedom to the flexible wick 207, so as to allow a range of adjustment thereof, while wick tail 215 assures complete utilization of all the liquid in the container 205. This degree of freedom permits self-adjustment of the wick relative to the surface of the orifice plate, to compensate for variations in position resulting from the vagaries of manufacture, and provides for a compliant feed means for transfer of the liquid from the container to the face of the orifice plate. As will be apparent to one skilled in the art, the height of the wick, as shown in FIGS. 6 and 7, may be adjusted to vary the liquid gap 214, as shown in FIG. 7, and to assure an appropriate degree of contact between the wick and the plate. For a more detailed view of the relationship between the wick and the orifice plate, attention is directed to FIG. 7, a magnified detail of a section of FIG. 6, wherein is shown the looped wick 207, in juxtaposition with domed orifice plate 203, thereby creating a liquid gap 214, in which the liquid to be transferred is in surface tension contact with the orifice plate. While FIG. 7 shows the wick and the plate as not actually in contact, it is to be understood that this gap is for illustration only, and that plate 203 does in fact contact the wick 207 for transfer of the liquid. As shown, the passage of the wick 207 through the opening 209 in the closure element 208 is controlled by the wick holder/positioner 210. FIG. 7 also shows the mounting grommet 204 for the piezoelectric element 202, orifice plate 203, and the orifice plate flange 212, as well as the clips 206 which hold the removable cap (not shown) to the bottle closure 208.

Figure 8:
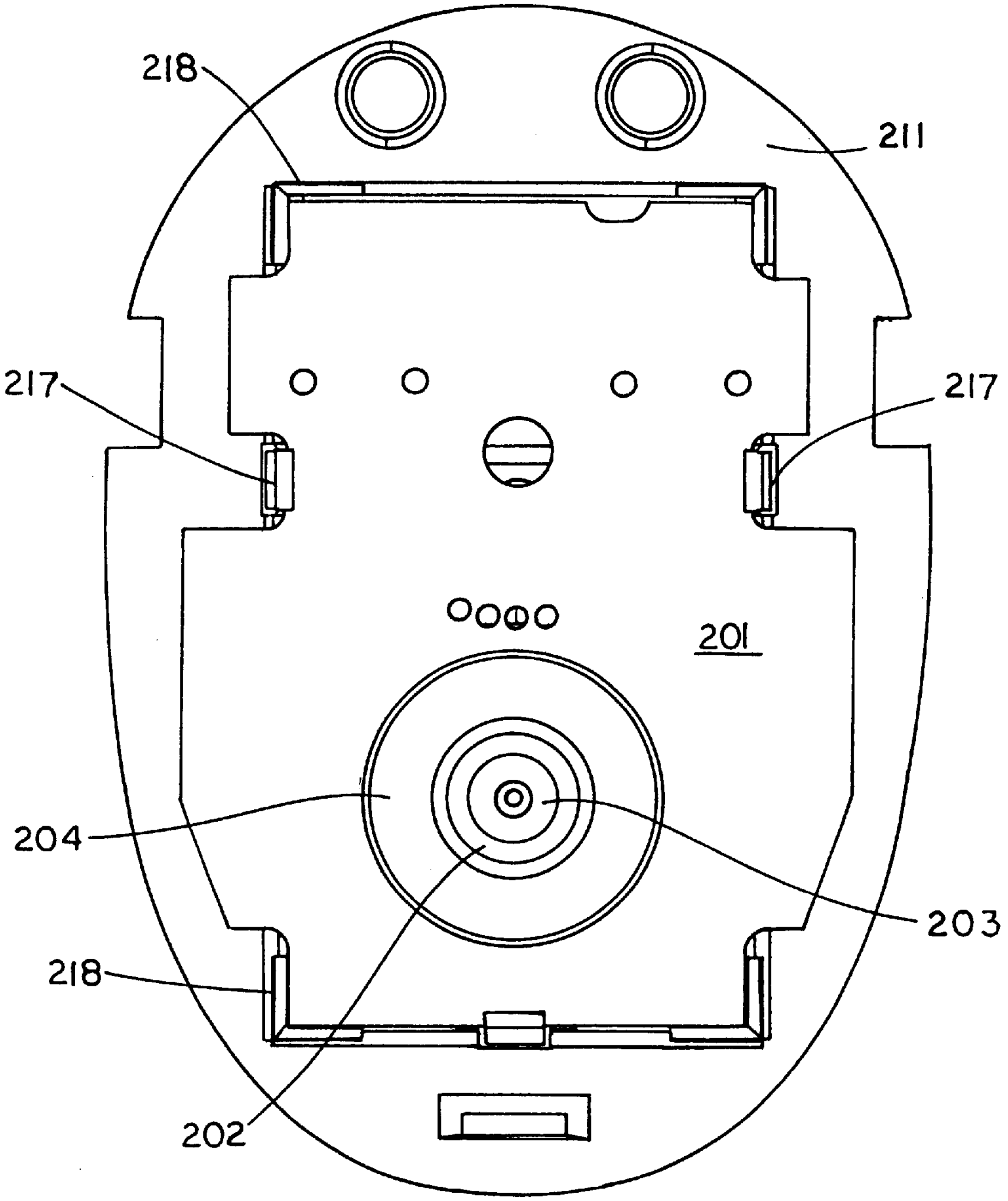
FIG. 8 is a top view of the piezoelectric element and the printed circuit board mounted on the chassis of a preferred embodiment.

FIG. 8 is a top view, showing the relationship of circuit board 201, piezoelectric element 202, orifice plate 203, mounting grommet 204, and the chassis board 211. As previously indicated, the piezoelectric element 202, in annular relationship to the orifice plate 203, is held in place in the circuit board 201 by the grommet 204. The circuit board is mounted on chassis board 211 in conventional manner, such as with clips 217 and positioning brackets 218.

Figure 9:
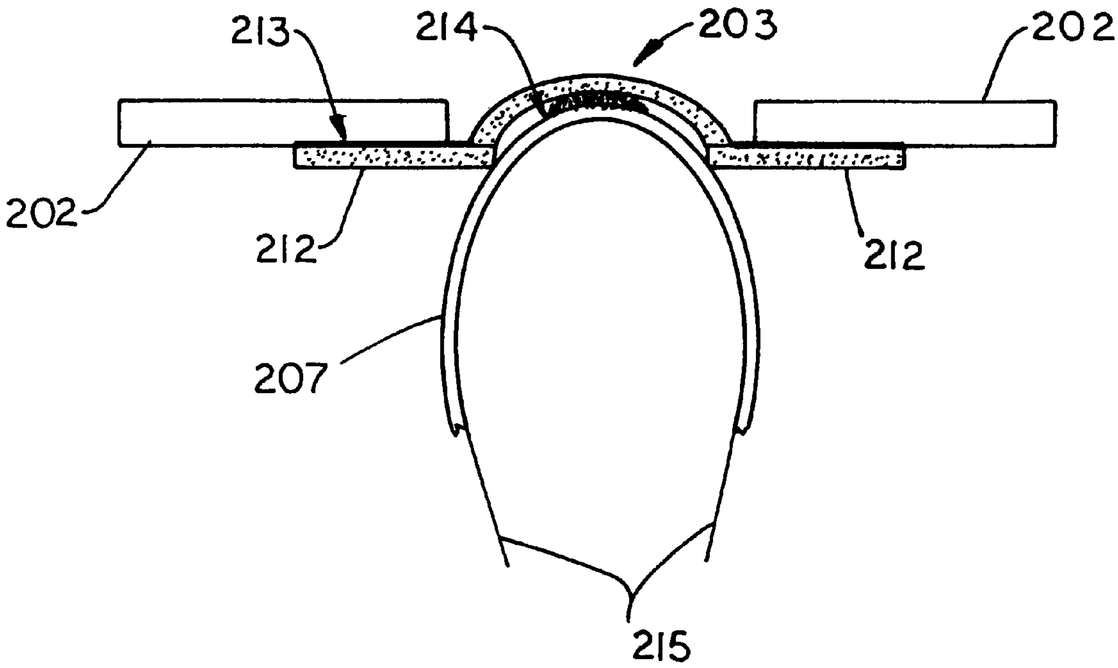
FIG. 9 illustrates a much simplified cross-sectional diagram of a piezoelectric pump assembly suitable for use with a preferred embodiment of the present invention.

In FIG. 9, a simplified cross sectional diagram of the invention illustrates the overall relationship of various elements. The orifice plate 203 is shown as including orifice plate flanges 212, which are in turn attached to the piezoelectric element 202 by suitable attachment means 213, such as epoxy adhesive. The wick 207 is illustrated in partial contact with the orifice plate 203, creating liquid gap 214, by which the liquid to be dispensed is transferred to the orifice plate. The wick is shown as also comprising fabric tails 215, which extend into the liquid container 205, not shown.

Figure 10:
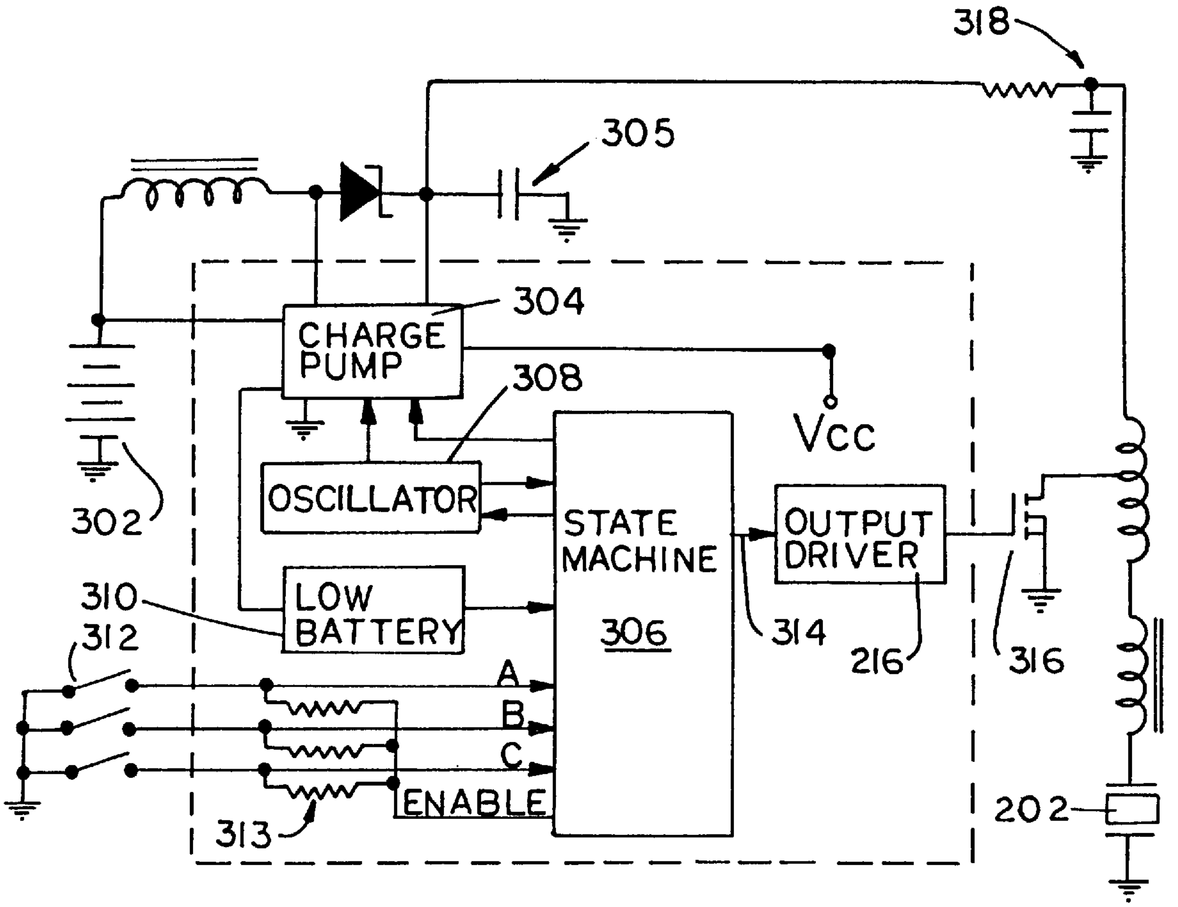
FIG. 10 is a block diagram of a preferred control circuit for driving the piezoelectric element.

The piezoelectric element 202 is controlled by control circuitry on the circuit board 201 to provide consistent performance over an extended period. With reference to FIG. 10 the control circuitry is implemented by an application specific integrated circuit (ASIC) 300 which receives power from a battery 102. The battery 302 is connected to a charge pump 304 which, together with external components 305, acts as a DC-to-DC step up converter. Operation of the charge pump is controlled by a state machine 306 which receives timing signals from an oscillator 308 which produces a 20 MHz clock signal, for example, that is applied to the charge pump 304. The state machine also receives an indication from a low battery indicator circuit 310.

The functionality of the control circuit, and specifically the state machine 306 is determined by a set of three selector switches 312 which produce input signals A, B, C to the state machine 306. The state machine inputs from the selector switches 312 are connected to individual pull-up resistors 313 which are selectively coupled to the positive supply voltage Vcc by the ENABLE signal from the state machine 306. This allows the voltage to be disconnected from the pull-up resistors 313 to conserve battery power during inactive periods of the control circuit. As will be described, the operation of state machine produces an output signal on line 314 which has an amplitude and a 301 frequency for driving the piezoelectric element 202. That output signal on line 314 is coupled through an output driver 216 to produce the output of the ASIC 300. The output driver 216 controls the conductive state of metal oxide field effect transistor (MOSFET) 316 which in turn controls the flow of electric current from the charge pump 304 to the piezoelectric element 202.

Figure 11:
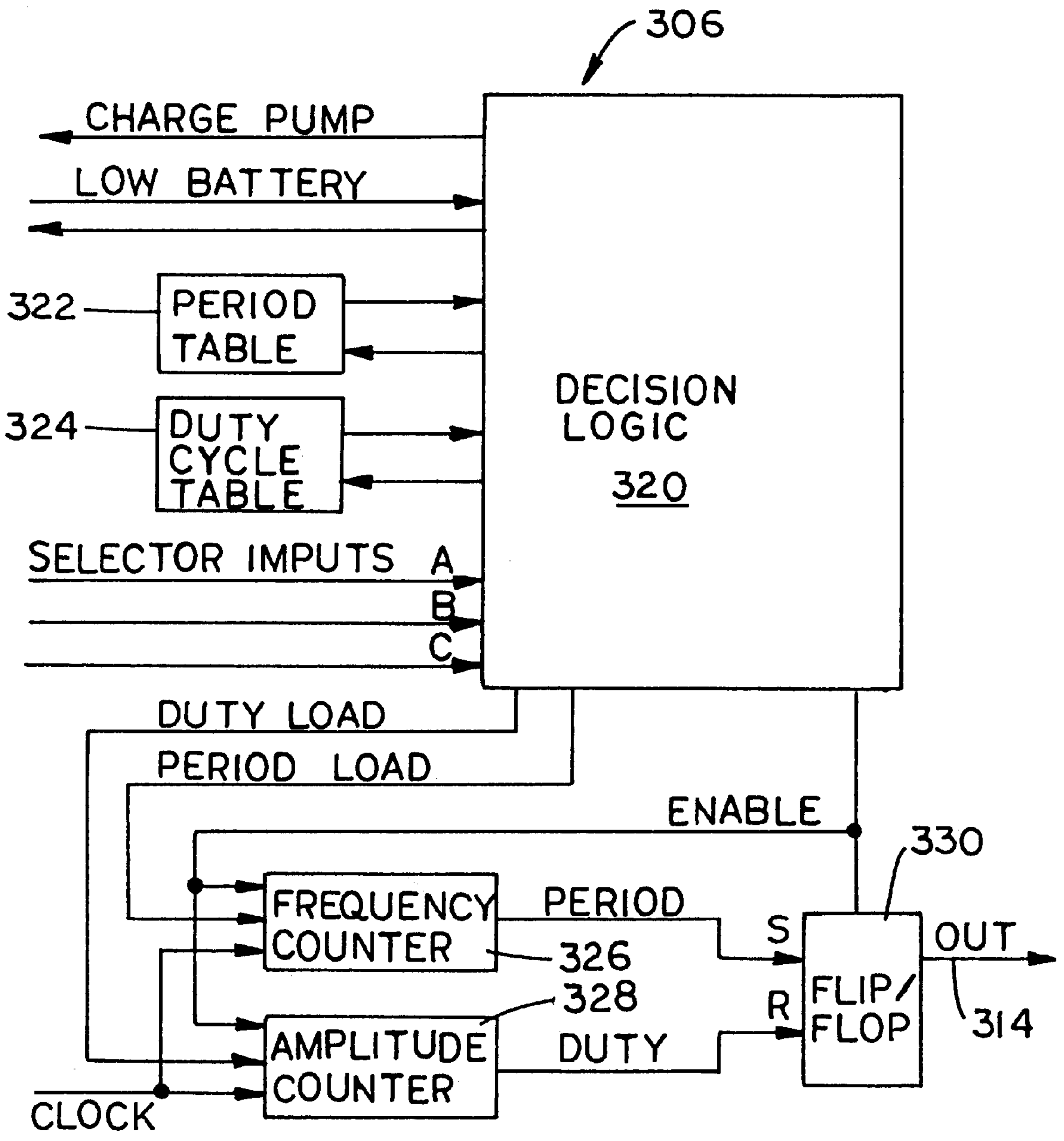
FIG. 11 illustrates the details of the state machine in FIG. 10.

The details of the state machine 306 are shown in FIG. 11. The preferred embodiment of the state machine 306 utilizes hardware circuity in an application specific integrated circuit but alternatively could be implemented by a programmable device such as a microprocessor and associated circuitry. The state machine 306 has decision logic 320 to which the selector input A, B and C are applied. The decision logic 306 also is interfaced to storage devices 322 and 324 which respectively contain data regarding the period and the duty cycle for the output signal that drives the piezoelectric element 202. The decision logic selects appropriate period and duty cycle values from the storage devices 322 and 324, respectively and transfers them to the preload inputs of a frequency counter 326 and an amplitude counter 328, respectively. These counters 326 and 328 receive a clock signal from the oscillator 308 and are enabled by a signal from the decision logic 320. As will be described, when the frequency counter 326 counts down to zero, it produces an output pulse designated PERIOD which is applied to the set of a flip/flop 330. Similarly, when the amplitude counter 328 reaches zero, it produces a DUTY signal that is the reset input of flip/flop 330. The flip/flop is enabled by the signal from the decision logic 320 and produces the output signal on line 314.

The driver circuit for the piezoelectric element 202 utilizes amplitude and frequency modulation to power the piezoelectric element 202 thus providing a portable, battery operated dispenser for continuous use in an air trephener or pesticide application. The circuitry allows extended operation utilizing a relatively low-voltage battery 302 and provides a range of ingredient delivery rates. The circuit drives the piezoelectric element 202 with amplitude and frequency modulation utilizing an intermittent duty cycle. The electronic-circuit is programmable and can be used to set a precise atomizing delivery rate in milligrams per hour. This is accomplished by selector switch 312 that allows the user to adjust the off time between cycles and thus change the intensity/effectiveness to a desired level based on personal preference or for different room sizes. It has been discovered that the dispenser's performance is directly related to the excitation voltage of the piezoelectric element 102. However, it was also discovered that with increased voltage, the dispenser utilized the limited battery energy less efficiently. Therefore, by varying the amplitude of the excitation voltage from a high level to a low level, the delivery performance was enhanced without incurring reduced efficiency. This result was due to the momentary high level excitation that initiates the atomization in a "high-performance" mode. Thereafter, lower level excitations are merely necessary to maintain that level of performance.

The present inventors also found that the optimum operating frequency for the piezoelectric element 202, varied from unit to unit due to what are believed to be manufacturing differences in the circuitry and the dispenser components, such as the piezoelectric element 202. This phenomenon can be overcome by sweeping the excitation frequency through a predefined range thereby compensating for the unit-to-unit variations.

Another feature of the present driver circuitry is to provide a constant delivery of active ingredients regardless of the state of the battery charge. This circuitry includes a portion 318 that accumulates adequate charge to pulse the piezoelectric element 202. As the battery voltage decays, the circuit insures that the proper amount of energy is available for a consistent pump action. When the battery voltage decays to the point that the circuit can no longer provide the proper energy, the circuitry turns the unit off. Thus, the circuitry provides a constant output delivery regardless of the state of charge of the battery 302. When the battery voltage decays to the point that a constant delivery output is not possible, the dispenser turns off.

During the operation of the dispenser, the control circuit spends most of its time in a low-power mode, commonly referred to as a sleep state. In the sleep state, the signal from the oscillator 308 is driving a timer within the decision logic 320 of the state machine 306. During this sleep state, the output signal on line 314 of the state machine is a low logic level thereby rendering the piezoelectric element 102 inactive. The period of the sleep state is determined by the settings of the rate selector switch 312 and the particular inputs A, B and C to the state machine 306. The relationship between the switch settings and the resultant signals A, B and C is shown in Table A.

| INPUTS | | | STATE OF |
|---|---|---|---|
| A | B | C | OPERATION |
| CLOSED | OPEN | OPEN | UNIT OFF |
| OPEN | OPEN | CLOSED | UNIT ON, SLEEP TIME = 18 SECS |
| OPEN | OPEN | OPEN | UNIT ON, SLEEP TIME = 27 SECS |
| CLOSED | CLOSED | OPEN | UNIT ON, SLEEP TIME = 27 SECS |
| CLOSED | OPEN | CLOSED | UNIT ON, SLEEP TIME = 27 SECS |
| OPEN | CLOSED | CLOSED | UNIT ON, SLEEP TIME = 27 SECS |
| CLOSED | CLOSED | CLOSED | UNIT ON, SLEEP TIME = 27 SECS |
| OPEN | CLOSED | OPEN | UNIT ON, SLEEP TIME = 36 SECS |

TABLE A

If the rate selector switch 312 is set so that the dispenser is off or when the low battery circuit 240 detects that the charge on the battery 302 had drained to a point where normal operation is not possible, the modulation sequence is not performed and the dispenser enters an inactive state.

Figure 12:
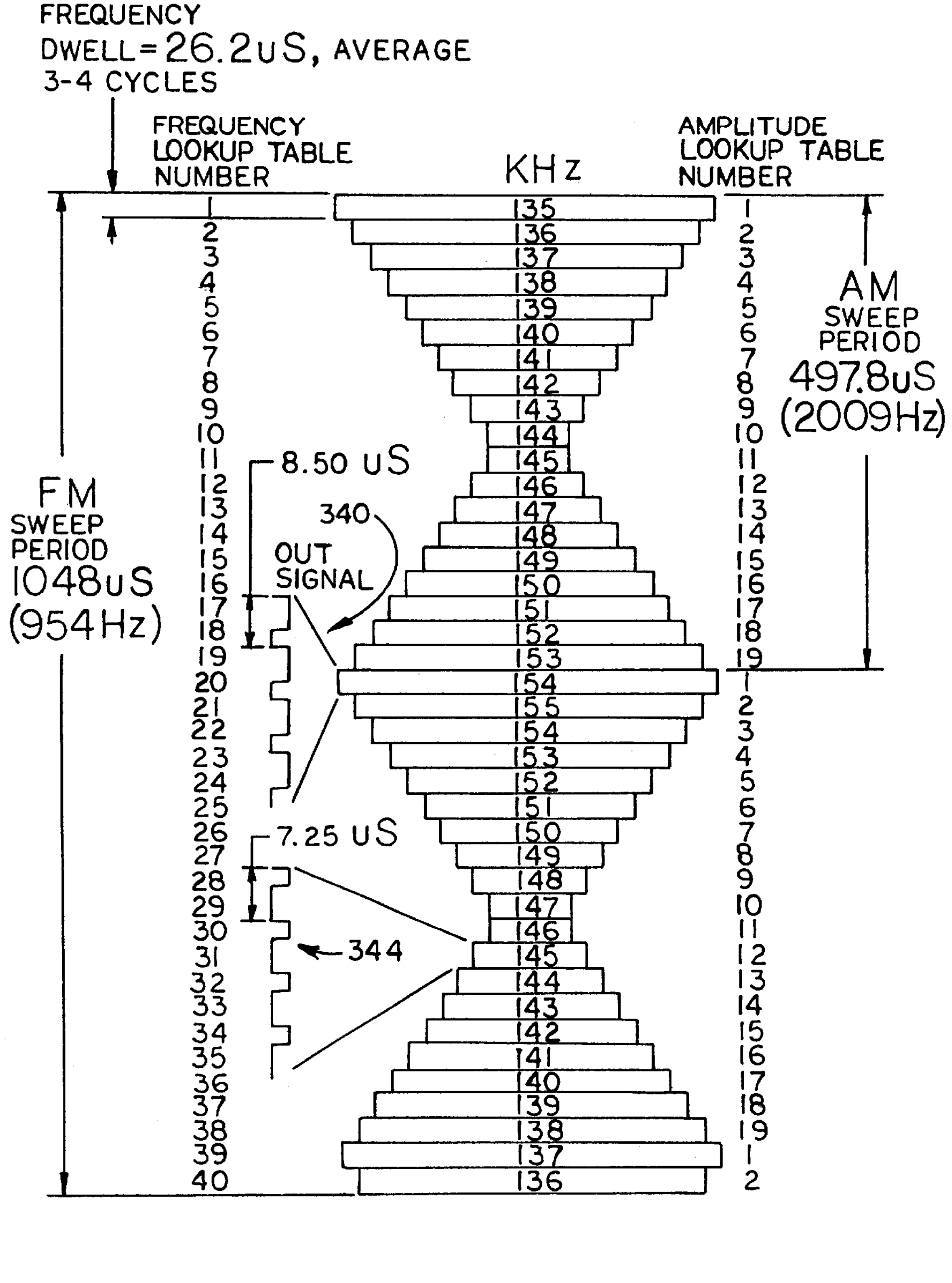
FIG. 12 graphically depicts the modulation of the output signal of the control circuit.

When the dispenser is on and the state machine 306 wakes up, it produces a brief output signal which drives the piezoelectric element 102. The state machine 306 generates a signal for driving the piezoelectric element that sweeps through a range of frequencies and a range of amplitudes. In the preferred embodiment, there are 19 amplitude values stored in the duty cycle table 322 and 40 frequency values stored in the period table. The decision logic 320 has an internal timer which every 26.2 microsecond causes the amplitude and frequency values in the next set of table locations to be retrieved and loaded in the two counters 326 and 328. Since the number of discrete amplitude and frequency values are different the amplitude changes so that as a given frequency is periodically used to drive the piezoelectric element 102 its amplitude also varies. This concept is depicted in FIG. 12 where as the frequency sweeps through the 40 values (135 kHz to 155 kHz) in the period table 322 the amplitude is swept though 19 values from the duty cycle table 324. Note that since 40 is not evenly divisible by 19, when the frequency sweep repeats the first frequency (135 kHz) will have an amplitude value of 3.

This process is accomplished by the decision logic 306 in FIG. 11 enabling the frequency and amplitude counters 326 and 328. The counters 326 and 328 control the period and the duty cycle of the alternating signal on output line 314. In essence, the two eight-bit preloadable counters 326 and 328 divide the 20 MHz clock signal produced by oscillator 308 by the values from the two tables 322 and 324 to control the period and duty cycle of the output signal. The frequency counter divides the 20 MHz clock signal down to between 135 KHz and 155 KHz. Every 26.2 microsecond the decision logic resets the counter by obtaining the next frequency value from the period table 322 and loading that value via the preload count line into frequency counter 326. This reloads the counter 326 with the proper countdown value.

At the same time a new duty cycle value is obtained from the table 324 and loaded into the amplitude counter 328. The duty cycle values vary the pulse width of the output signal on line 314 between 1.4 microseconds and 5.0 microseconds. This duty cycle controls the amplitude of the output signal and a longer time period gives a greater amplitude.

The output signal on line 314 is a digital signal which is applied through output driver 216 to control the conductive state of a power MOSFET 316. The counters 326 and 328 control the operation of Flip/Flop 314 which produces a square wave output signal that varies in frequency and duty cycle as determined by the two counters 326 and 328, and shown at 340 and 344 in FIG. 12.

While the present invention has been described with respect to what are at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions.

INDUSTRIAL APPLICABILITY

The atomization systems of this invention, which are described in the present application can be used to automatically dispense such liquids as air fresheners, perfumes, or insecticides, to any given environment, over an extended period of time, with the advantage of uniformly dispensing equal amounts of liquid to the atmosphere over the life span of the battery which drives the dispenser. Further, the dispenser may be reused at will by means of refills and replacement batteries, so that the consumer may change the liquid being dispersed to the atmosphere as desired, with the added advantage that the amount of liquid being dispersed may be varied to adjust intensity or effectiveness to a desired level for personal preference, efficacy, or for room size.

What is claimed is:

1. A method for operating a battery powered vibratory liquid atomizer of the type in which an orifice plate, to which liquid to be atomized is supplied, vibrates to drive the liquid from its surface in the form of a small liquid particles during drive periods which occur alternately with sleep periods, said method comprising:

vibrating said orifice plate at the beginning of each drive period at a relatively high amplitude sufficient to clear a film of liquid from an outer surface of said orifice plate, to initiate atomization of the liquid; and thereafter vibrating said orifice plate at a relatively low amplitude sufficient to sustain the atomization during the remainder of the drive period.

2. A method according to claim 1 wherein, after vibrating the orifice plate at a relatively low amplitude, terminating the vibration of said orifice plate for a predetermined duration and thereafter repeating the steps of vibrating the orifice plate at a higher amplitude and then at a lower amplitude.

3. A method according to claim 1 wherein, said steps of vibrating said orifice plate are carried out by vibrating said orifice plate at amplitudes which decreases in a generally exponential manner with time.

4. A method according to claim 1 wherein said orifice plate is part of a vibrating system which has a natural resonant frequency and wherein said plate is vibrated at a frequency which is varied over a range which includes a harmonic of said natural resonant frequency.

5. A method according to claim 1 wherein, the frequency of vibration is swept several times over said frequency range during the carrying out of said steps.

6. A method of energizing a battery driven piezoelectric vibrating liquid atomizer of the type in which a piezoelectric actuating element with an alternating voltage to expand and contract and thereby to vibrate an orifice plate to which a liquid to be atomized is supplied, so that vibration of said orifice plate atomizes said liquid and ejects it from the orifice plate in the form of fine aerosolized particles during drive periods which occur alternately with sleep periods, said method comprising:

during a drive period, first applying a high amplitude alternating voltage to said piezoelectric actuating element to cause it to vibrate said orifice plate at a high amplitude to clear from an outer surface thereof, a film of liquid which had accumulated thereon during a previous sleep period, to initiate atomization of the liquid; and thereafter, for the remainder of said drive period, applying a lower alternating voltage to said piezoelectric actuating element to sustain said atomization during said remainder of said drive period.

7. A method according to claim 6 wherein, said steps of applying a high alternating voltage and thereafter applying a lower alternating voltage are carried out once during a drive period which is followed by a sleep period and wherein said steps are repeated during a subsequent drive period following said sleep period.

8. A method according to claim 7, further including, during a drive period, a step of varying a frequency of said alternating voltage over a frequency range which includes a harmonic of a natural resonant frequency of a vibrating system which includes said orifice plate.

9. A method according to claim 8 wherein, the step of varying the frequency of said alternating voltages is carried out by sweeping the frequency of said alternating voltages back and forth over said frequency range several times during said drive period.

10. A method according to claim 7 wherein, the steps of first applying a high alternating voltage and thereafter applying a lower alternating voltage are carried out by charging a capacitor during periods between successive drive periods, allowing said capacitor to discharge during said drive periods, generating alternating voltages corresponding to the voltage across said capacitor during said drive periods, and applying said alternating voltages to said piezoelectric element.

11. A method according to claim 7 wherein, the steps of first applying a high alternating voltage and thereafter applying a lower alternating voltage to said piezoelectric actuator element are carried out by applying a decreasing direct current voltage to one end of a coil whose other end is connected to said piezoelectric actuator element and at the same time rapidly connecting and disconnecting a minor portion of said coil, which is nearest to its said one end, to and from ground at a high rate during each drive period.

12. A method according to claim 11 wherein, said rapidly connecting and disconnecting is carried out at a variable frequency which includes a harmonic of a natural resonant frequency of a system which includes said orifice plate and said piezoelectric actuator.

13. A method according to claim 11, wherein said connecting extends for first durations and said disconnecting extends for second durations, said first durations being equal to each other and said second durations being different from each other.

14. A method according to claim 11 wherein, said steps of connecting and disconnecting are initiated following each sleep period and extend for a predetermined drive period.

15. A method according to claim 7 wherein, the steps of first applying a high alternating voltage includes the steps of connecting a battery through a coil and a diode to a capacitor and successively connecting and disconnecting a point between said coil and said diode to and from ground to charge said capacitor to a regulated voltage which is higher than the voltage of said battery.

16. A method according to claim 15, wherein the duration required to charge said capacitor greatly exceeds that of a drive period.

17. A method according to claim 15, further including a step of measuring a further duration during which said connecting and disconnecting charges said capacitor to said regulated voltage, and, in response to said further duration exceeding a predetermined amount, connecting said battery to ground to fully discharge same.

18. A method according to claim 17, further including the step of preventing further application of alternating voltages to said piezoelectric actuation element in response to said connecting and disconnecting exceeding a predetermined duration.

19. A method according to claim 6 wherein, said steps of initially applying a high alternating voltage and thereafter applying a lower alternating voltage are carried out by applying to said piezoelectric actuating element, an alternating voltage which is initially high and which decreases at a generally exponential rate.

20. A vibratory liquid atomizer comprising:

an orifice plate;

a liquid conduit arranged to supply liquid to be atomized to said orifice plate; and a vibration actuator coupled to said orifice plate and connected to vibrate said orifice plate at a high amplitude at the beginning of a drive period to initiate atomization of the liquid and thereafter, for the remainder of said drive period, to vibrate said orifice plate at a lower amplitude sufficient to sustain the atomization.

21. a vibratory liquid atomizer according to claim 20, wherein said vibration actuator includes a controller which, after said drive period, terminates vibration of said orifice plate for a predetermined duration and thereafter vibrates the orifice plate first at a high amplitude and then at a lower amplitude.

22. A vibratory liquid atomizer according to claim 21 wherein, said controller is configured to vibrate said orifice plate at amplitudes which decrease in a generally exponential manner with time during said drive period.

23. A vibratory liquid atomizer according to claim 21 wherein, said controller includes a frequency sweep element connected to cause said orifice plate to vibrate in a manner such that, its frequency of vibration varies over a frequency range which includes a harmonic of a natural resonant frequency of a vibrating system which includes said orifice plate.

24. A vibratory liquid atomizer according to claim 23 wherein, said frequency sweep element is constructed to cause the frequency of vibration to be swept several times over said frequency range during said drive period.

25. A vibratory liquid atomizer comprising:

an orifice plate mounted to be vibrated;

a liquid supply conduit arranged to supply liquid to said orifice plate while it is vibrating;

a piezoelectric actuating element coupled to said orifice plate to cause it to vibrate when said element expands and contracts; and an electric power supply system connected to supply an alternating voltage to said actuating element during a drive period to cause it to expand and contract and thereby to vibrate said orifice plate to atomize said liquid and eject it in the form of fine aerosolized liquid particles, said electric power supply system including circuits connected to apply a high alternating voltage to said piezoelectric actuating element at the beginning of said drive period to cause it to vibrate said orifice plate at a high amplitude sufficient to initiate atomization of the liquid and thereafter, for the remainder of said drive period, to apply a lower alternating voltage to said piezoelectric actuating element to sustain said atomization.

26. A vibratory liquid atomizer according to claim 25 wherein, said electric power supply system includes timers and switches connected and arranged to terminate the application of alternating voltages to said actuator during a sleep period following said drive period and thereafter to resume the application of alternating voltages to said actuator during a successive drive period.

27. A vibratory liquid atomizer according to claim 26 wherein, said power supply system includes a voltage supply circuit capable of supplying a voltage which is initially high at the onset of a drive period and which decreases at a generally exponential rate during said drive period.

28. A vibratory liquid atomizer according to claim 25 wherein, said power supply system includes a variable frequency oscillator circuit having a frequency sweep range which includes a harmonic of a natural resonant frequency of a vibrating system which includes said orifice plate and wherein said oscillator circuit is connected to apply variable frequency signals to said actuator element.

29. A vibratory liquid atomizer according to claim 28 wherein, the frequency sweep rate of said variable frequency oscillator is such that the frequency of said alternating voltages is swept back and forth over said frequency range several times during said drive period.

30. A vibratory liquid atomizer according to claim 25 wherein, said power supply system includes a charge supply capacitor and charging and timing circuits connected to recharge said charge supply capacitor during time periods between successive drive periods, said charge supply capacitor being connected to discharge while supplying driving voltage to said piezoelectric actuator during said drive periods, and further including an alternating voltage generator circuit for generating alternating voltages corresponding to the discharging voltage across said capacitor during said drive periods, and for applying said alternating voltages to said piezoelectric element.

31. A vibratory liquid atomizer according to claim 25 wherein, said power supply system includes a coil, one end of which is connected to a source of decreasing voltage and the other end of which is connected to said piezoelectric actuator, and a switching circuit connected to rapidly connect and disconnect a minor portion of said coil, which is nearest to said one end thereof, to and from ground at a high rate during each drive period.

32. A vibratory liquid atomizer according to claim 31 wherein, said switching circuit is connected to be operated by an oscillator whose frequency is such that said rapid connecting and disconnecting is carried out at a variable rate which includes the natural resonant frequency of a system which includes said orifice plate and said piezoelectric actuator.

33. A vibratory liquid atomizer according to claim 31 wherein, said switching circuit is arranged to cause said connecting and disconnecting to follow a pattern such that the durations of connecting said portion of said coil to ground are equal to each other and wherein the durations of disconnecting said portion of said coil from ground vary.

34. A vibratory liquid atomizer according to claim 31 wherein, said switching circuit which is connected to rapidly connect and disconnect a minor portion of said coil, is arranged to be started following each sleep period and to extend for a predetermined drive period.

35. A vibratory liquid atomizer according to claim 25 wherein, said power supply system includes a battery, a coil a diode and a capacitor connected in series with each other and connected to supply current to a charge supply capacitor, a switch connected from a point between said coil and said diode to ground, and a switch operation circuit connected to successively open and close said switch when the voltage on said charge supply capacitor drops below a first, lower, voltage and to hold said switch open when the voltage on said charge supply capacitor exceeds a second, higher, voltage.

36. A vibratory liquid atomizer according to claim 35 wherein, said coil and said charge supply capacitor are of a size such that the charging of said charge supply extends over a period which greatly exceeds a drive period of said atomizer.

37. A vibratory liquid atomizer according to claim 35, wherein, said power supply system further includes a timer connected to measure the duration of said successive opening and closing of said switch and, in response to said duration exceeding a predetermined amount, connecting said battery to ground to fully discharge same.

38. A vibratory liquid atomizer according to claim 37, further including a further switch arranged to be operated in response to the duration of said opening and closing of said switch exceeding a predetermined amount, said further switch being connected such that upon operation thereof, the supply of alternating voltages to said actuation element is terminated.

* * * * *